(12) United States Patent
Holmes

(10) Patent No.: US 11,992,329 B2
(45) Date of Patent: May 28, 2024

(54) PROCESSING OPTICAL COHERENCE TOMOGRAPHY SCANS

(71) Applicant: MICHELSON DIAGNOSTICS LIMITED, Maidstone (GB)

(72) Inventor: Jonathan Denis Holmes, West Maling (GB)

(73) Assignee: MICHELSON DIAGNOSTICS LTD., Maidstone (GB)

( * ) Notice: Subject to any disclaimer, the term of this patent is extended or adjusted under 35 U.S.C. 154(b) by 351 days.

(21) Appl. No.: 17/620,052

(22) PCT Filed: Jun. 19, 2020

(86) PCT No.: PCT/IB2020/055763
§ 371 (c)(1),
(2) Date: Dec. 16, 2021

(87) PCT Pub. No.: WO2020/255048
PCT Pub. Date: Dec. 24, 2020

(65) Prior Publication Data
US 2022/0304620 A1 Sep. 29, 2022

(30) Foreign Application Priority Data
Jun. 19, 2019 (GB) ...................... 1908766

(51) Int. Cl.
G06N 3/08 (2023.01)
A61B 5/00 (2006.01)
(Continued)

(52) U.S. Cl.
CPC ............ *A61B 5/443* (2013.01); *A61B 5/0066* (2013.01); *A61B 5/0077* (2013.01);
(Continued)

(58) Field of Classification Search
CPC ......... G09B 23/286; A61B 8/46; A61B 5/442; A61B 5/443; A61B 5/1075; A61B 34/20;
(Continued)

(56) References Cited

U.S. PATENT DOCUMENTS 7,907,772 B2 * 3/2011 Wang ..................... A61N 5/103
382/128
2009/0306520 A1 12/2009 Schmitt et al.
(Continued)

FOREIGN PATENT DOCUMENTS

CN 107993221 A 5/2018
EP 3065086 A1 9/2016
(Continued)

OTHER PUBLICATIONS

International Search Report and Written Opinion for Application No. PCT/IB2020/055763 dated Sep. 17, 2020.
(Continued)

*Primary Examiner* — Phuoc H Doan
(74) *Attorney, Agent, or Firm* — Burns & Levinson LLP; Steven M. Mills

(57) ABSTRACT

A method of processing optical coherence tomography (OCT) scans through a subject's skin, the method comprising: receiving at least a plurality of OCT scans through the subject's skin (7), each scan representing an OCT signal in a slice through the subject's skin (7), with the plurality of OCT scans being spaced apart such that the OCT scans represent the OCT signal through a volume through the subject's skin; processing each OCT scan using a processor so as to so as to detect at least one three dimensional structure in the skin; classifying, using a processor, the structure as belonging to a class of a plurality of classes of structures; and outputting at least one of the structure and the class.

20 Claims, 4 Drawing Sheets

(51) Int. Cl.
  *A61B 5/107* (2006.01)
  *G06T 7/00* (2017.01)
  *G06T 7/11* (2017.01)
  *G06T 7/73* (2017.01)
  *G06V 20/69* (2022.01)

(52) U.S. Cl.
  CPC .......... *A61B 5/0082* (2013.01); *A61B 5/1075* (2013.01); *A61B 5/442* (2013.01); *A61B 5/489* (2013.01); *G06T 7/0012* (2013.01); *G06T 7/11* (2017.01); *G06T 7/73* (2017.01); *G06V 20/698* (2022.01); *A61B 2576/02* (2013.01); *G06T 2207/10101* (2013.01); *G06T 2207/20081* (2013.01); *G06T 2207/20092* (2013.01); *G06T 2207/30088* (2013.01); *G06T 2207/30096* (2013.01); *G06T 2207/30101* (2013.01)

(58) Field of Classification Search
  CPC ........... G06T 7/12; G06T 7/162; A61G 13/09; G06V 20/698
  See application file for complete search history.

(56) References Cited

U.S. PATENT DOCUMENTS

2012/0274898 A1 11/2012 Sadda et al.
2019/0110739 A1* 4/2019 Tey ...................... G06T 7/0012

FOREIGN PATENT DOCUMENTS

| GB | 2515761 A | 1/2015 |
| GB | 2549515 A | 10/2017 |
| RU | 2007131190 A | 8/2007 |
| WO | 2017171643 A1 | 10/2017 |
| WO | 2019104217 A1 | 5/2019 |
| WO | 2019104221 A1 | 5/2019 |

OTHER PUBLICATIONS

Search Report for Application No. GB1908766.7 dated Nov. 22, 2019.
Welzel, "Optical coherence tomography in dermatology: a review," Skin Research and Technology, 2001; 7:1-9.

* cited by examiner

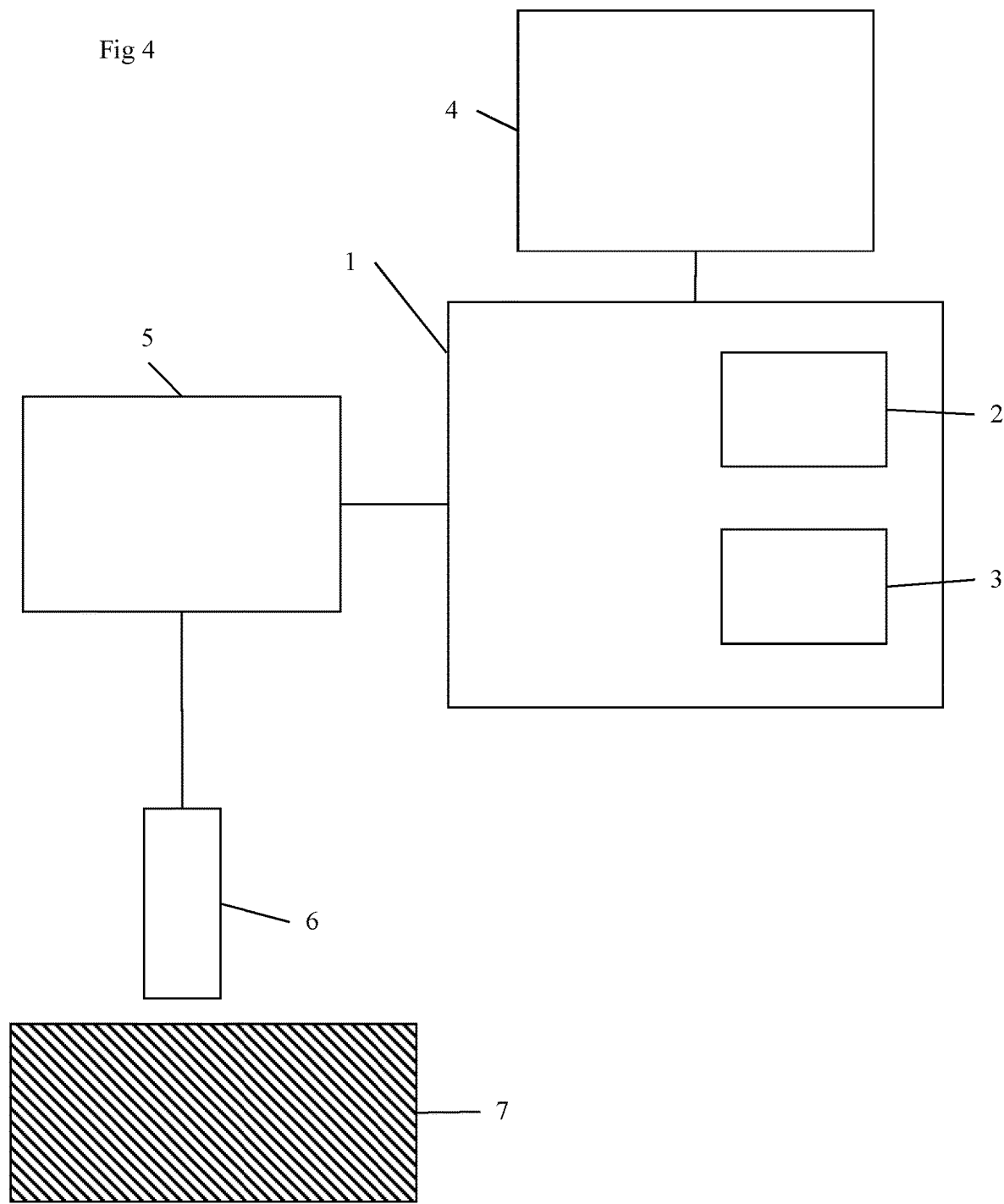

PROCESSING OPTICAL COHERENCE TOMOGRAPHY SCANS

CROSS-REFERENCE TO RELATED APPLICATIONS

This application is a U.S. national stage application under 35 U.S.C. 371 of co-pending International Application No. PCT/IB2020/055763, filed Jun. 19, 2020, entitled PROCESSING OPTICAL COHERENCE TOMOGRAPHY SCANS, which in turn claims priority to Great Britain Patent Application No. GB1908766.7, filed Jun. 19, 2019, the entire contents of which are incorporated by reference herein for all purposes.

This invention relates to processing optical coherence tomography (OCT) scans.

Optical Coherence Tomography (OCT) was invented in 1991 at MIT in the USA and is commonly used for imaging human tissue of various organs, in particular the eye, and also skin (J. Welzel, "Optical coherence tomography in dermatology: a review," *Skin Research and Technology*, vol. 7, pp. 1-9. 2001).

Those skilled in the art will be familiar with the VivoSight OCT device, manufactured and marketed by Michelson Diagnostics Ltd of Maidstone, Kent, United Kingdom, which is designed for use by professional dermatologists in the assessment of skin lesions of patients. The VivoSight OCT device scans the skin and presents to the user images of the skin subsurface structure, in a plane perpendicular to the skin surface. This is known as a 'B-scan'.

Also, VivoSight can acquire scans at multiple locations across the skin surface in order to build up a series of B-scans across a lesion of interest. This is known as a multi-slice 'stack' and can be viewed by the user in a variety of ways to elicit tissue features of medical interest such as nests of cancer cells. For example, the user can view the stack of B-scans in rapid succession to 'fly through' the lesion area.

However, it is desirable to aid the users of such apparatus in determining features within the structure of the skin, rather than simply displaying the scans to the user an allowing them to interpret the images as shown to them. This would reduce the size of the 'learning curve' for clinicians to make use of the apparatus, make the procedure faster and more convenient and help the clinician find the features of most interest.

According to a first aspect of the invention, there is provided a method of processing optical coherence tomography (OCT) scans through a subject's skin, the method comprising:

- receiving at least a plurality of OCT scans through the subject's skin, each scan representing an OCT signal in a slice through the subject's skin, with the plurality of OCT scans being spaced apart such that the OCT scans represent the OCT signal through a volume through the subject's skin;
- processing each OCT scan using a processor so as to so as to detect at least one three dimensional structure in the skin;
- classifying, using a processor, the structure as belonging to a class of a plurality of classes of structures; and
- outputting at least one of the structure and the class.

As such, this invention provides for an automatic determination of structures found in a subject's skin, and makes use of the three-dimensional nature of an OCT scan of a volume of a subject's skin.

Typically, the method could comprise generating a confidence with which the structure can be assigned to the class of structures. The method could comprise generating a confidence with which the structure could be assigned to a plurality, or all, of the plurality of classes of structures.

The method may comprise segmenting the subject's skin within the OCT scan or scans; the segmentation may be of the volume and so be carried out in three dimensions. The segmentation may comprise the segmentation of the skin into different components (for example, epidermis, dermis, hair follicles and so on). The segmentation may determine the position of the structure relative to the components of the subject's skin. The step of classifying may use the position of the structure relative to the components of the subject's skin to classify the structure as belonging to a class.

The step of classifying the structure, and optionally the step of detecting the structure, may comprise using a machine learning algorithm. Typically, the machine learning algorithm will previously have been trained to classify structures in a subject's skin; alternatively, the method may comprise training the machine learning algorithm. Machine learning algorithms are typically trained by providing them with known inputs—in this invention most likely OCT scans, or structures that have been identified in OCT scans—and an indication of what the correct classification of the known input is.

Example machine learning algorithms that may be employed include a convolutional neural net or a random forest algorithm.

The OCT scans may comprise dynamic OCT scans, in that they comprise time-varying OCT scans through the subject's skins. Such scans allow for the identification of in particular blood vessels in the subject's skin. The method may therefore comprise determining the position of blood vessels in dynamic OCT scans and typically using the position of the blood vessels relative to the structure in the step of classifying the structure.

The method may comprise capturing at least one image of the surface of the user's skin, typically using a camera, and using each image to classify the structure. The images may be captured using visible light and/or infrared light. For example, the method may comprise determining a pigment of the skin, and using that to classify the structure.

The method may comprise the determination of at least one numerical parameter of the skin. The at least one numerical parameter may comprise at least one parameter selected from the group comprising: optical attenuation coefficient, surface topography/roughness, depth of blood vessel plexus, blood vessel density. Each numerical parameter may be used in classifying the structure.

The method may comprise:
- processing the OCT data for each scan with depth to produce a indicative depth scan representative of the OCT signal at each depth through all of the scans;
- fitting a curve to the indicative depth scan, the curve comprising a first term which exponentially decays with respect to the depth and a second term which depends on the noise in the OCT signal; and
- calculating a compensated intensity for the uncompensated OCT signal at each point through each scan, the compensated intensity comprising a ratio of a term comprising a logarithm of the OCT signal to a term comprising the fitted curve.

The method may comprise using the compensated intensity to classify the structure. A problem with using uncompensated intensity to classify the structure is that the intensity associated with a given structure depends upon the depth of the structure within the tissue due to the scattering and absorption of the tissue above it; this dependence of intensity on depth makes the classification process more difficult; whereas structures in images with compensated intensity exhibit depth-dependence to a much lesser degree and so may be more easily classified.

The plurality of classes of structures may be selected from the group comprising:
basal cell carcinoma (BCC)
squamous cell carcinoma (SCC)
actinic keratosis (AK)
seborrheic keratosis (SebK)
benign nevus
dysplastic nevus
hair follicle
blood vessel
cyst
sebaceous gland
melanoma The method may comprise allowing a user to select which structures are in the plurality of classes. This will assist a user if they are unsure which of a selection of structures a particular structure might be. Alternatively, the user may simply indicate that the plurality of classes may be any from a set that the processor is programmed to recognise.

The step of outputting may comprise outputting any features of the OCT scans which contributed as part of the classification of the structure as belonging to the class. As such, a user can then see why a particular structure was so classified. The method may comprise allowing a user to reject some of the features, in which case the method may then repeat the step of classifying the structure without using the rejected features.

In accordance with a second aspect of the invention, there is provided an optical coherence tomography (OCT) image processing apparatus, comprising a processor, a display coupled to the processor and storage coupled to the processor, the storage carrying program instructions which, when executed on the processor, cause it to carry out the method of the first aspect of the invention.

The image processing apparatus may comprise an OCT apparatus by means of which the OCT scans are captured. As such, the image processing apparatus may comprise an OCT probe arranged to generated interferograms, and the processor may be arranged to generate the images from the interferograms. As such, the image processor may be arranged to process the images as they are captured.

Alternatively, the image processing apparatus may be separate from any OCT apparatus and may be arranged to process the images subsequent to their capture. As such the image processing apparatus may comprise data reception means (such as a network connection or media drive) arranged to receive the OCT scans for processing.

There now follows, by way of example only, description of an embodiment of the invention, described with reference to the accompanying drawings, in which:

FIG. 4 shows schematically the optical coherence tomography (OCT) apparatus used in FIGS. 1a to 3b.

Figure 1A:
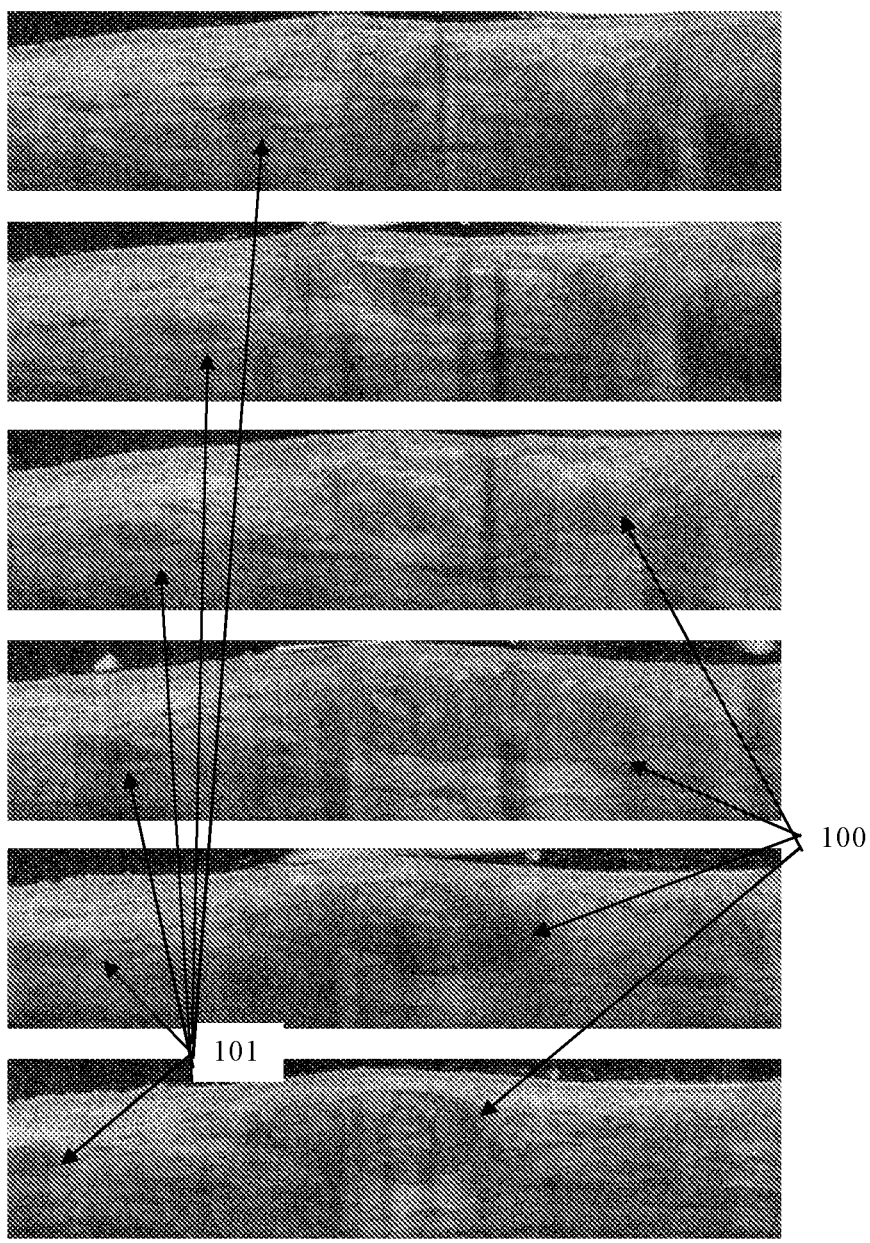
FIG. 1a shows a selection of OCT scans through a stack captured with an OCT apparatus in accordance with an embodiment of the invention.

An optical coherence tomography (OCT) apparatus in accordance with an embodiment of the invention is shown in FIG. 4 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft® Windows® or Apple® Mac OS X® can be used. The computer 1 is also provided with a display 4 controlled by the processor 2 on which any desired graphics can be displayed.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight® apparatus available from Michelson Diagnostics of Maidstone, Kent, United Kingdom.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin. By taking many parallel scans, a three-dimensional stack of bitmaps can be built up.

The processor can then be used to process the OCT scans taken. The probe is used to capture scans of the subject's skin and the data is transmitted to the image processor unit in the form of a 'stack' of B-scans. Each B-scan is an image of the skin at a small perpendicular displacement from the adjacent B-scan. Typically and preferably, the stack comprises 120 B-scan images, each of which is 6 mm wide by 2 mm deep, with a displacement between B-scans of 50 microns.

Figure 1B:
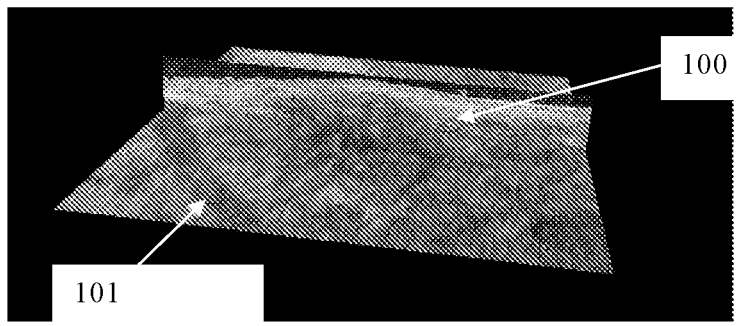
FIG. 1b shows a 3D projection of the stack of images from which the images of FIG. 1a were selected.

FIGS. 1a and 1b show representations of such an image stack. For clarity, only 6 of the 120 images are shown with spacing of 400 microns between them. In the sequence of images shown in FIG. 1a can be seen a tumour (the large ellipsoidal dark grey object) and also a large dilated blood vessel (smaller ellipsoidal dark grey object). In the sequence of images it is notable that the blood vessel appears in successive images at different x-positions, whereas the tumour does not. Those skilled in the art will be aware that in any individual image, it is not easy to distinguish the vessel ellipsoid from a tumour ellipsoid, based on shape alone; however in the sequence of displaced images the three-dimensional shape of the vessel can be discerned as a linear structure that is quite different from the irregular tumour shape.

In FIG. 1b, there is shown a 3D projection of the stack, with the vessel and tumour indicated by arrows.

Figure 2A:
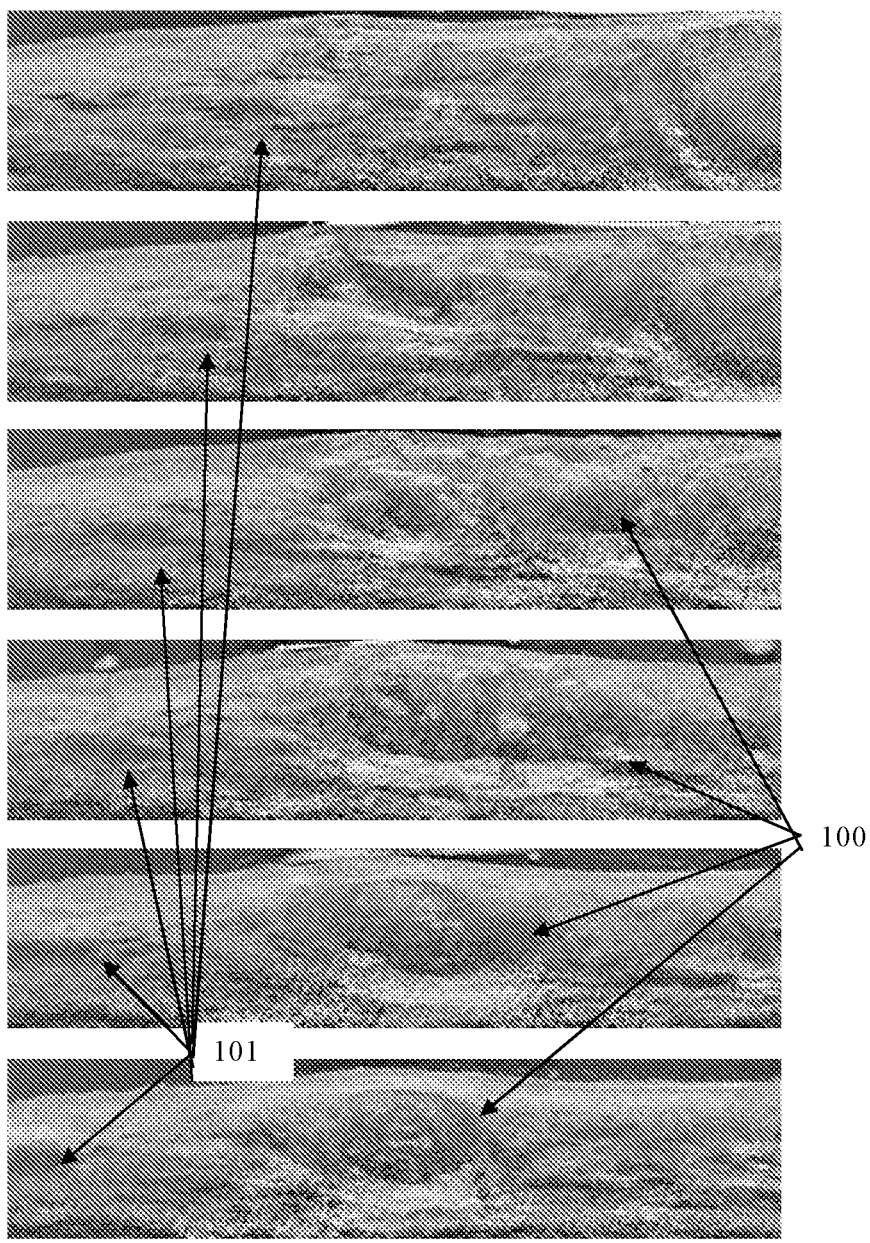
FIGS. 2a and 2b show the same selection of scans and 3D projection as FIGS. 1a and 1b, in which depth compensation has been applied by the OCT apparatus.
Figure 2B:
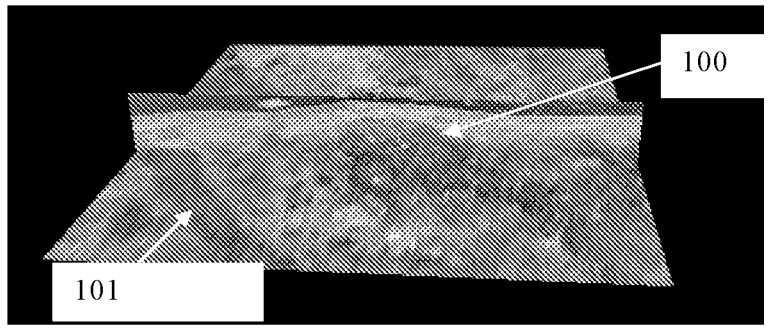

These raw images are first processed to compensate for attenuation of OCT signal with depth and then filtered to reduce the amount of noise and image clutter. The optical attenuation compensation method is disclosed in the PCT application published as WO2017/182816. The filtering is the median filter which is well known to those skilled in the art. The resulting processed images are shown in FIGS. 2a and 2b, which respectively show a selection of images from the stack and a 3D projection of the stack.

Figure 3A:
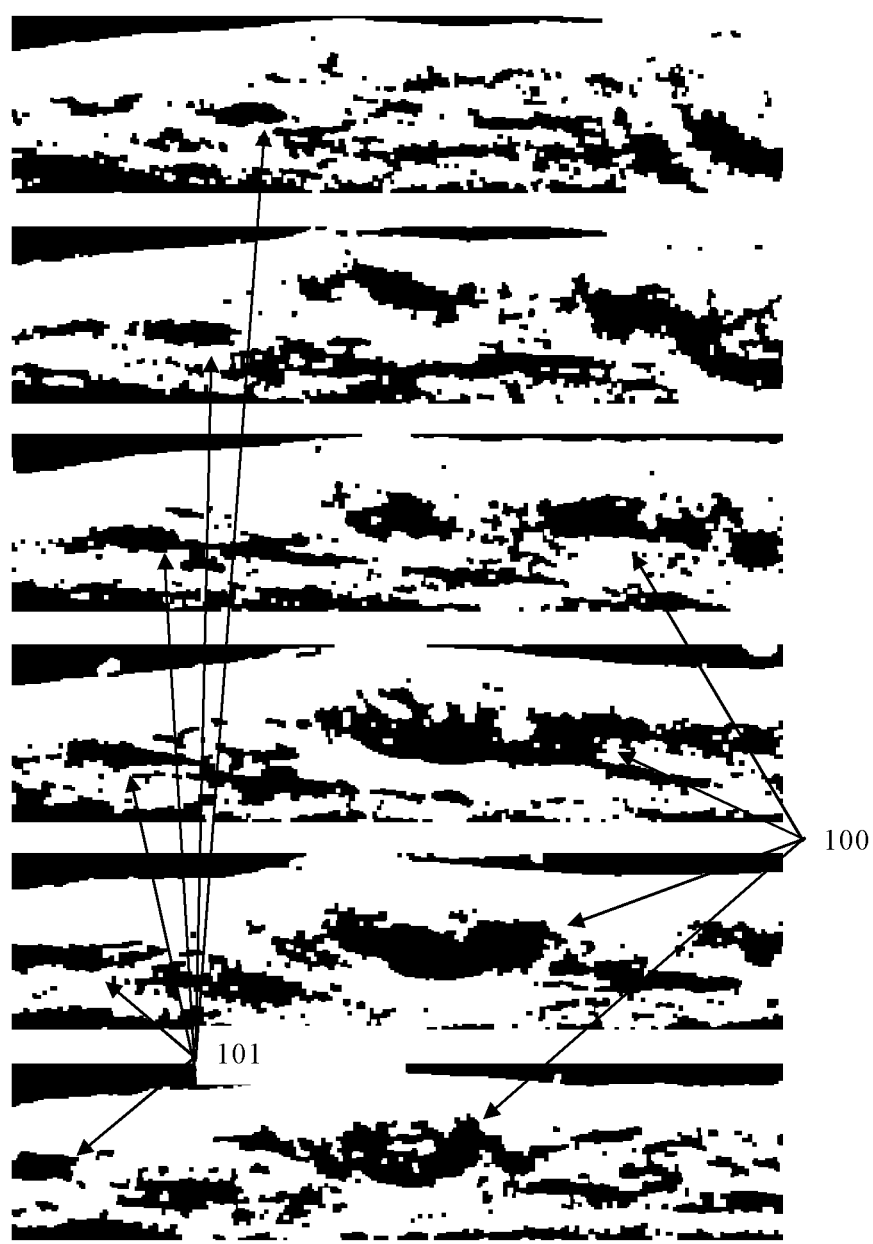
FIGS. 3a and 3b show the same selection of scans and 3D projection as FIGS. 1a and 1b, in which a binary morphology operation has been applied.
Figure 3B:
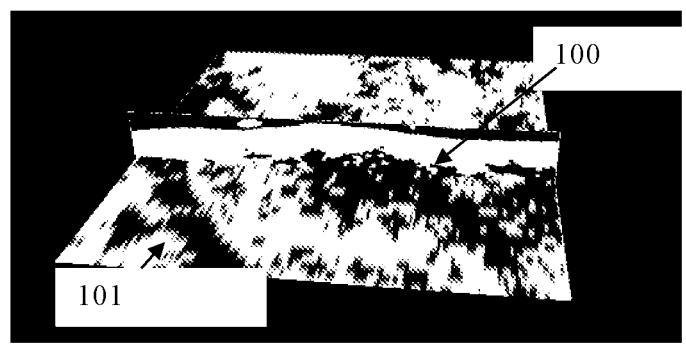

The next step carried out is a binary threshold operation and further denoising of the image by performing an 'open' and 'close' binary morphology operation on the image stack. The results are shown in FIGS. 3a and 3b, which again respectively show a selection of images from the stack and a 3D projection of the stack.

This image stack is then processed to segment and extract all of the individual 3-dimensional objects present in the stack that have continguous interconnected regions. The features of each such object are extracted, namely the horizontal length and width, vertical size, total volume, surface area, depth of the object centroid, ellipticity and density. This is not an exhaustive list and others may also be found to be useful.

These object features are fed into a Random Forest machine learning algorithm, or alternatively a neural network, which has been taught with many such examples of scans of skin with benign or malignant growths. It will be appreciated that the vessel in this example has completely different feature results from the tumour and so it is easy to unambiguously distinguish the vessel from the tumour. The vessel object is elongated in 3-dimensional space and located deep in the dermis, whereas the tumour is irregularly shaped in three dimensions and located at a shallow depth in the dermis. By placing the vessel object into a class of deep, highly elongated objects, and the tumour object into a class of shallow, irregular objects, the classifier is able to correctly identify the former as a benign vessel and the latter as a malignant basal cell carcinoma.

The invention claimed is:

1. A method of processing optical coherence tomography (OCT) scans through a subject's skin, the method comprising:
   receiving at least a plurality of OCT scans through the subject's skin, each scan representing an OCT signal in a slice through the subject's skin, with the plurality of OCT scans being spaced apart such that the OCT scans represent the OCT signal through a volume through the subject's skin;
   processing each OCT scan using a processor so as to detect at least one three dimensional structure in the skin;
   classifying, using a processor, the structure as belonging to a class of a plurality of classes of structures; and
   outputting at least one of the structure and the class.

2. The method of claim 1, comprising generating a confidence with which the structure can be assigned to the class of structures, which may be output in the step of outputting.

3. The method of claim 2, comprising generating a confidence with which the structure could be assigned to a plurality of the classes in the plurality of classes.

4. The method of claim 1, comprising segmenting the subject's skin within the OCT scan into different components, in which the segmentation is of the volume and is carried out in three dimensions.

5. The method of claim 4, in which the segmentation determines the position of the structure relative to the components of the subject's skin and the step of classifying uses the position of the structure relative to the components of the subject's skin to classify the structure as belonging to a class.

6. The method of claim 1, in which the step of classifying the structure, and optionally the step of detecting the structure, comprises using a machine learning algorithm.

7. The method of claim 1, in which the OCT scans comprise dynamic OCT scans, in that they comprise time-varying OCT scans through the subject's skins, and the method comprises determining the position of blood vessels in the dynamic OCT scans and using the position of the blood vessels relative to the structure in the step of classifying the structure.

8. The method of claim 1, comprising capturing at least one image of the surface of the user's skin, typically using a camera, and using each image to classify the structure.

9. The method of claim 8, in which the images are captured using at least one of visible light and infrared light.

10. The method of claim 8, comprising determining a pigment of the skin, and using the pigment to classify the structure.

11. The method of claim 1, comprising the determination of at least one numerical parameter of the skin and using each numerical parameter in classifying the structure.

12. The method of claim 11, in which the at least one numerical parameter comprises at least one parameter selected from the group comprising: optical attenuation coefficient, surface topography/roughness, depth of blood vessel plexus, and blood vessel density.

13. The method of claim 1, comprising:
   processing the OCT data for each scan with depth to produce a indicative depth scan representative of the OCT signal at each depth through all of the scans;
   fitting a curve to the indicative depth scan, the curve comprising a first term which exponentially decays with respect to the depth and a second term which depends on the noise in the OCT signal; and
   calculating a compensated intensity for the uncompensated OCT signal at each point through each scan, the compensated intensity comprising a ratio of a term comprising a logarithm of the OCT signal to a term comprising the fitted curve.

14. The method of claim 13, comprising using the compensated intensity to classify the structure.

15. The method of claim 14, in which the compensated intensity is used together with the uncompensated intensity in classifying the structure.

16. The method of claim 1, in which the plurality of classes of structures are selected from the group comprising:
   basal cell carcinoma (BCC);
   squamous cell carcinoma (SCC);
   actinic keratosis (AK);
   seborrheic keratosis (SebK);
   benign nevus;
   dysplastic nevus;
   hair follicle;
   cyst;
   sebaceous gland; and
   melanoma.

17. The method of claim 1, comprising allowing a user to select which structures are in the plurality of classes.

18. The method of claim 1, in which the step of outputting comprises outputting any features of the OCT scans which contributed as part of the classification of the structure as belonging to the class.

19. The method of claim 18, comprising allowing a user to reject some of the features which contributed, and repeating the step of classifying the structure without using the rejected features.

20. An optical coherence tomography (OCT) image processing apparatus, comprising a processor, a display coupled to the processor and storage coupled to the processor, the storage carrying program instructions which, when executed on the processor, cause it to carry out the method of claim 1.

\* \* \* \* \*